US006879656B2

(12) United States Patent
Cesmeli et al.

(10) Patent No.: US 6,879,656 B2
(45) Date of Patent: Apr. 12, 2005

(54) METHOD AND APPARATUS FOR DERIVING MOTION INFORMATION FROM PROJECTION DATA

(75) Inventors: Erdogan Cesmeli, Brookfield, WI (US); Peter Michael Edic, Albany, NY (US)

(73) Assignee: General Electric Company, Schenectady, NY (US)

(*) Notice: Subject to any disclaimer, the term of this patent is extended or adjusted under 35 U.S.C. 154(b) by 77 days.

(21) Appl. No.: 10/624,342

(22) Filed: Jul. 22, 2003

(65) Prior Publication Data

US 2004/0125908 A1 Jul. 1, 2004

Related U.S. Application Data

(60) Provisional application No. 60/397,658, filed on Jul. 23, 2002, and provisional application No. 60/398,463, filed on Jul. 25, 2002.

(51) Int. Cl.[7] .................................................. A61B 6/00
(52) U.S. Cl. .............................. 378/4; 378/901; 378/19
(58) Field of Search ................................. 378/4, 81, 15, 378/16, 19, 162, 901

(56) References Cited

U.S. PATENT DOCUMENTS

| 5,552,605 A | * | 9/1996 | Arata | 250/363.04 |
| 5,561,695 A | * | 10/1996 | Hu | 378/8 |
| 5,640,436 A | * | 6/1997 | Kawai et al. | 378/4 |
| 6,539,074 B1 | * | 3/2003 | Yavuz et al. | 378/4 |

* cited by examiner

Primary Examiner—David V. Bruce
Assistant Examiner—Irakli Kiknadze
(74) Attorney, Agent, or Firm—Fletcher Yoder

(57) ABSTRACT

One or more techniques are provided for deriving motion data from a set of CT projection data. The techniques calculate moments associated with consistency conditions for the projection data to derive motion data from the projection data. One aspect of the present techniques uses the calculated moments to select projection data sets based upon the presence or absence of motion between the projection data sets. Periodicity information may then be extracted from the selected projection data sets. Another aspect of the present techniques uses projection data acquired by a slowly rotating volumetric CT gantry to allow the separation of a corruptive signal from a desired motion signal. Once separated, the desired motion signal may be used to identify projection data at a desired phase of motion.

68 Claims, 7 Drawing Sheets

METHOD AND APPARATUS FOR DERIVING MOTION INFORMATION FROM PROJECTION DATA

CROSS-REFERENCE TO RELATED APPLICATIONS

This application claims the benefit of U.S. Provisional Application No. 60/397,658 filed on Jul. 23, 2002 and U.S. Provisional Application 60/398,463 filed on Jul. 25, 2002.

BACKGROUND OF THE INVENTION

The present invention relates generally to the field of medical imaging and more specifically to the field of imaging dynamic, internal tissue, such as cardiac tissue, by computed tomography. In particular, the present invention relates to the generation of a signal representative of internal motion using projection data.

Computed tomography (CT) imaging systems measure the attenuation of X-ray beams passed through a patient from numerous angles. Based upon these measurements, a computer is able to reconstruct images of the portions of a patient's body responsible for the radiation attenuation. As will be appreciated by those skilled in the art, these images are based upon separate examination of a series of angularly displaced projection images. A CT system processes X-ray projection data to generate 2D maps of the line integral of linear attenuation coefficients of the scanned object at multiple view angle positions. These data are then reconstructed to produce an image, which is typically displayed on a monitor, and may be printed or reproduced on film. A virtual 3-D image may also be produced by a CT examination.

CT scanners operate by projecting fan shaped or cone shaped X-ray beams from an X-ray source. The X-ray beams may be collimated to control the shape and spread of the beams. The X-ray beams are attenuated as they pass through the object to be imaged, such as a patient. The attenuated beams are detected by a set of detector elements. Each detector element produces a signal affected by the attenuation of the X-ray beams, and the data are processed to produce signals that represent the line integrals of the attenuation coefficients of the object along the X-ray paths. These signals are typically called "projection data" or just "projections". By using reconstruction techniques, such as filtered backprojection, useful images may be formulated from the projections. The images may in turn be associated to form a volume rendering of a region of interest. The locations of regions of interest, such as pathologies, may then be identified either automatically, such as by a computer-assisted detection (CAD) algorithm or, more conventionally, such as by a trained radiologist. CT scanning provides certain advantages over other types of techniques in diagnosing disease, particularly because it illustrates the accurate anatomical information about the body. Further, CT scans may help physicians distinguish between types of abnormalities more accurately.

CT imaging techniques, however, may present certain challenges when imaging dynamic internal tissues, such as the heart. For example, in cardiac imaging, the motion of the heart causes inconsistencies in the projection data, which, after reconstruction, may result in various motion-related image artifacts such as blurring, streaking, or discontinuities. In particular, artifacts may occur during cardiac imaging when projections that are not acquired at the same point in the heart cycle, i.e., the same phase, are used to reconstruct the image or images that comprise the volume rendering.

To avoid the image artifacts associated with cardiac motion, therefore, it is desirable to reconstruct projection data acquired at the same phase into the desired images. This may be done by gating the acquisition of the projection data (prospective gating), or by methods that cull the projection data after acquisition (retrospective gating). For example, retrospective gating refers to selecting the projection data acquired at the same cardiac phase for image reconstruction. Typically, a simultaneously acquired electrocardiogram (ECG) signal is used to select projection data at a common phase of cardiac motion. Prospective gating refers to modulating data acquisition, such as the X-ray tube output and projection data acquisition, in response to real-time measurement and analysis of the ECG signal, i.e., acquiring only the projections of interest at a specified phase of cardiac motion for reconstruction.

However, an ECG signal is a measure of the depolarization and repolarization of the cardiac muscle tissue, and does not actually represent the motion of the tissue. While the electrical cardiac events measured by an ECG are generally indicative of cardiac muscle contraction and motion, the ECG is still only an indirect indicator of cardiac motion. Because of the indirect nature of this relationship, artifacts may still be present in the images reconstructed using gating techniques that rely upon ECG signals. It is desirable, therefore, to devise an indicator or signal that is directly related to cardiac motion for use in gating techniques or other techniques that would benefit from knowledge of the actual internal motion.

BRIEF DESCRIPTION OF THE INVENTION

The present technique provides a novel method and apparatus for determining the motion of an internal tissue or organ undergoing dynamic movement. Particularly, the technique provides for a method and system for processing acquired projection data to determine the motion. The motion information may in turn be used to facilitate data acquisition or image reconstruction, such as by gating techniques, to reduce or eliminate motion related artifacts.

In accordance with one aspect of the present technique, a method is provided for selecting a projection data set. The method comprises acquiring a set of projection data. At least one set of the 0th order moments, the 1st order moments, and the 2nd order moments of the set of projection data is calculated at different views positions for an axial location. A reference projection data set is selected from the projection data at the axial location and two or more comparison projection data sets are generated from the projection data at the axial location. A correlation error for each comparison projection data set relative to the reference projection data set is derived using the at least one set of moments and a matching projection data set is selected based upon the correlation errors.

In accordance with another aspect of the present technique, a computer program for selecting a projection data set is provided. The computer program may be provided on one or more computer readable media and may comprise a routine for acquiring a set of projection data. The program may also comprise a routine for calculating at least one set of the 0th order moments, the 1st order moments, and the 2nd order moments of the set of projection data at different views positions for an axial location. In addition, the program may comprise a routine for selecting a reference projection data set from the projection data at the axial location and a routine for generating two or more comparison projection data sets from the projection data at the axial location. A routine for deriving a correlation error for each comparison projection data set relative to the reference projection data set using the at least one set of moments and a routine for selecting a matching projection data set based upon the correlation errors may also be present.

In accordance with a further aspect of the present technique, a CT image analysis system is provided. The CT image analysis system may comprise an X-ray source configured to emit a stream of radiation and a detector configured to detect the stream of radiation and to generate one or more signals responsive to the stream of radiation. The detector may comprise a plurality of detector elements. The system may also comprise a system controller configured to control the X-ray source and to acquire a set of projection data from one or more of the detector elements via a data acquisition system and a computer system configured to receive the set of projection data. The computer system may be further configured to calculate at least one set of the 0th order moments, the 1st order moments, and the 2nd order moments of the set of projection data at different views positions for an axial location. In addition, the computer system may be configured to select a reference projection data set from the projection data at the axial location and to generate two or more comparison projection data sets from the projection data at the axial location. The computer system may be further configured to derive a correlation error for each comparison projection data set relative to the reference projection data set using the at least one set of moments and to select a matching projection data set based upon the correlation errors.

In accordance with an additional aspect of the present technique, a CT image analysis system is provided. The CT image analysis system may comprise an X-ray source configured to emit a stream of radiation and a detector configured to detect the stream of radiation and to generate one or more signals responsive to the stream of radiation. The detector may comprise a plurality of detector elements. The system may also comprise a system controller configured to control the X-ray source and to acquire a set of projection data from one or more of the detector elements via a data acquisition system and a computer system configured to receive the set of projection data. In addition, the system comprises means for calculating at least one set of moments of the set of projection data at different views positions for an axial location. The system also comprises means for selecting a reference projection data set from the projection data at the axial location and means for generating two or more comparison projection data sets from the projection data at the axial location. The system further comprises means for deriving a correlation error for each comparison projection data set relative to the reference projection data set using the at least one set of moments and means for selecting a matching projection data set based upon the correlation errors.

In accordance with another aspect of the present technique, a method for generating a motion signal from a set of projections is provided. The method comprises acquiring a set of projection data via a slowly rotating area detector and cone-beam radiation source. The 0th order moments for the set of projection data are calculated for each view position to form an aggregate motion signal. The aggregate motion signal is separated into a corruptive signal and a desired motion signal based on frequency characteristics.

In accordance with a further aspect of the present technique, a computer program for generating a motion signal from a set of projections is provided. The computer program may be provided on one or more computer readable media and may comprise a routine for acquiring a set of projection data via a slowly rotating area detector and cone-beam radiation source. The program may also comprise a routine for calculating the 0th order moments for the set of projection data for each view position to form an aggregate motion signal and a routine for separating the aggregate motion signal into a corruptive signal and a desired motion signal based on frequency characteristics.

In accordance with a further aspect of the present technique, a CT image analysis system is provided. The CT image analysis system may comprise a cone-beam X-ray source configured to emit a stream of radiation and an area detector configured to detect the stream of radiation and to generate one or more signals responsive to the stream of radiation. The detector may comprise a plurality of detector elements. The system may also comprise a system controller configured to slowly rotate the cone-beam X-ray source and the area detector and to acquire a set of projection data from one or more of the detector elements via a data acquisition system. The CT image analysis system may also comprise a computer system configured to receive the set of projection data. The computer system may be further configured to calculate the 0th order moments for the set of projection data for each view position to form an aggregate motion signal and to separate the aggregate motion signal into a corruptive signal and a desired motion signal based on frequency characteristics.

In accordance with a further aspect of the present technique, a CT image analysis system is provided. The CT image analysis system may comprise a cone-beam X-ray source configured to emit a stream of radiation and an area detector configured to detect the stream of radiation and to generate one or more signals responsive to the stream of radiation. The detector may comprise a plurality of detector elements. The system may also comprise a system controller configured to slowly rotate the cone-beam X-ray source and the area detector and to acquire a set of projection data from one or more of the detector elements via a data acquisition system. The CT image analysis system may comprise a computer system configured to receive the set of projection data. The CT image analysis system may also comprise means for forming an aggregate motion signal and means for separating the aggregate motion signal into a corruptive signal and a desired motion signal based on frequency characteristics.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
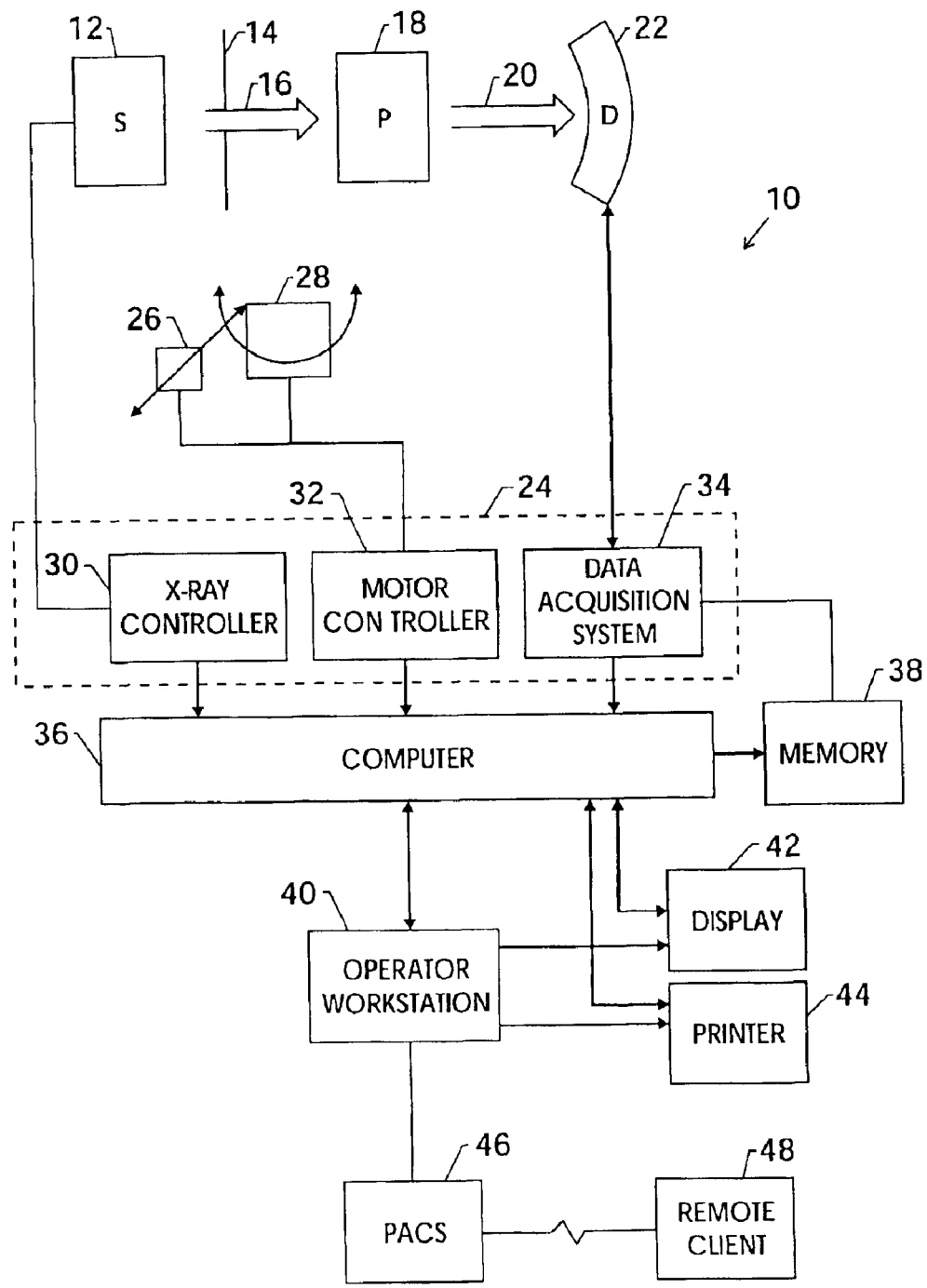
FIG. 1 is a diagrammatical view of an exemplary imaging system in the form of a CT imaging system for use in producing processed images, in accordance with one aspect of the present technique.

FIG. 1 illustrates diagrammatically an imaging system 10 for acquiring and processing image data. In the illustrated embodiment, system 10 is a computed tomography (CT) system designed to acquire X-ray projection data, to reconstruct the projection data into an image, and to process the image data for display and analysis in accordance with the present technique. In the embodiment illustrated in FIG. 1, imaging system 10 includes a source of X-ray radiation 12 positioned adjacent to a collimator 14. In this exemplary embodiment, the source of X-ray radiation source 12 is typically an X-ray tube.

Collimator 14 permits a stream of radiation 16 to pass into a region in which a subject, such as a human patient 18 is positioned. The stream of radiation 16 may be generally fan or cone shaped, depending on the configuration of the detector array, discussed below, as well as the desired method of data acquisition. A portion of the radiation 20 passes through or around the subject and impacts a detector array, represented generally at reference numeral 22. Detector elements of the array produce electrical signals that represent the intensity of the incident X-ray beam. These signals are acquired and processed to reconstruct an image of the features within the subject.

Source 12 is controlled by a system controller 24, which furnishes both power, and control signals for CT examination sequences. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 is coupled to a linear positioning subsystem 26 and rotational subsystem 28. The rotational subsystem 28 enables the X-ray source 12, collimator 14 and the detector 22 to be rotated one or multiple turns around the patient 18. It should be noted that the rotational subsystem 28 might include a gantry. Thus, the system controller 24 may be utilized to operate the gantry. The linear positioning subsystem 26 enables the patient 18, or more specifically a patient table, to be displaced linearly. Thus, the patient table may be linearly moved within the gantry to generate images of particular areas of the patient 18. Although the embodiment of the system described above is a third generation CT scanner, the methods to generate signals representative of cardiac motion described herein apply to all advanced generation CT systems.

Additionally, as will be appreciated by those skilled in the art, the source of radiation may be controlled by an X-ray controller 30 disposed within the system controller 24. Particularly, the X-ray controller 30 is configured to provide power and timing signals to the X-ray source 12. A motor controller 32 may be utilized to control the movement of the rotational subsystem 28 and the linear positioning subsystem 26.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a computer 36.

The computer 36 is typically coupled to the system controller 24. The data collected by the data acquisition system 34 may be transmitted to the computer 36 for subsequent processing and reconstruction. The computer 36 may comprise or communicate with a memory 38 that can store data processed by the computer 36 or data to be processed by the computer 36. It should be understood that any type of memory to store a large amount of data might be utilized by such an exemplary system 10. Moreover, the memory 38 may be located at the acquisition system or may include remote components for storing data, processing parameters, and routines described below.

The computer 36 may also be adapted to control features enabled by the system controller 24, i.e., scanning operations and data acquisition. Furthermore, the computer 36 may be configured to receive commands and scanning parameters from an operator via an operator workstation 40 typically equipped with a keyboard and other input devices (not shown). An operator may thereby control the system 10 via the input devices. Thus, the operator may observe the reconstructed image and other data relevant to the system from computer 36, initiate imaging, and so forth.

A display 42 coupled to the operator workstation 40 may be utilized to observe the reconstructed image. Additionally, the scanned image may also be printed by a printer 44 which may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 might be coupled to a remote system 48, radiology department information system (RIS), hospital information system (HIS) or to an internal or external network, so that others at different locations may gain access to the image data.

It should be further noted that the computer 36 and operator workstation 40 may be coupled to other output devices, which may include standard, or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
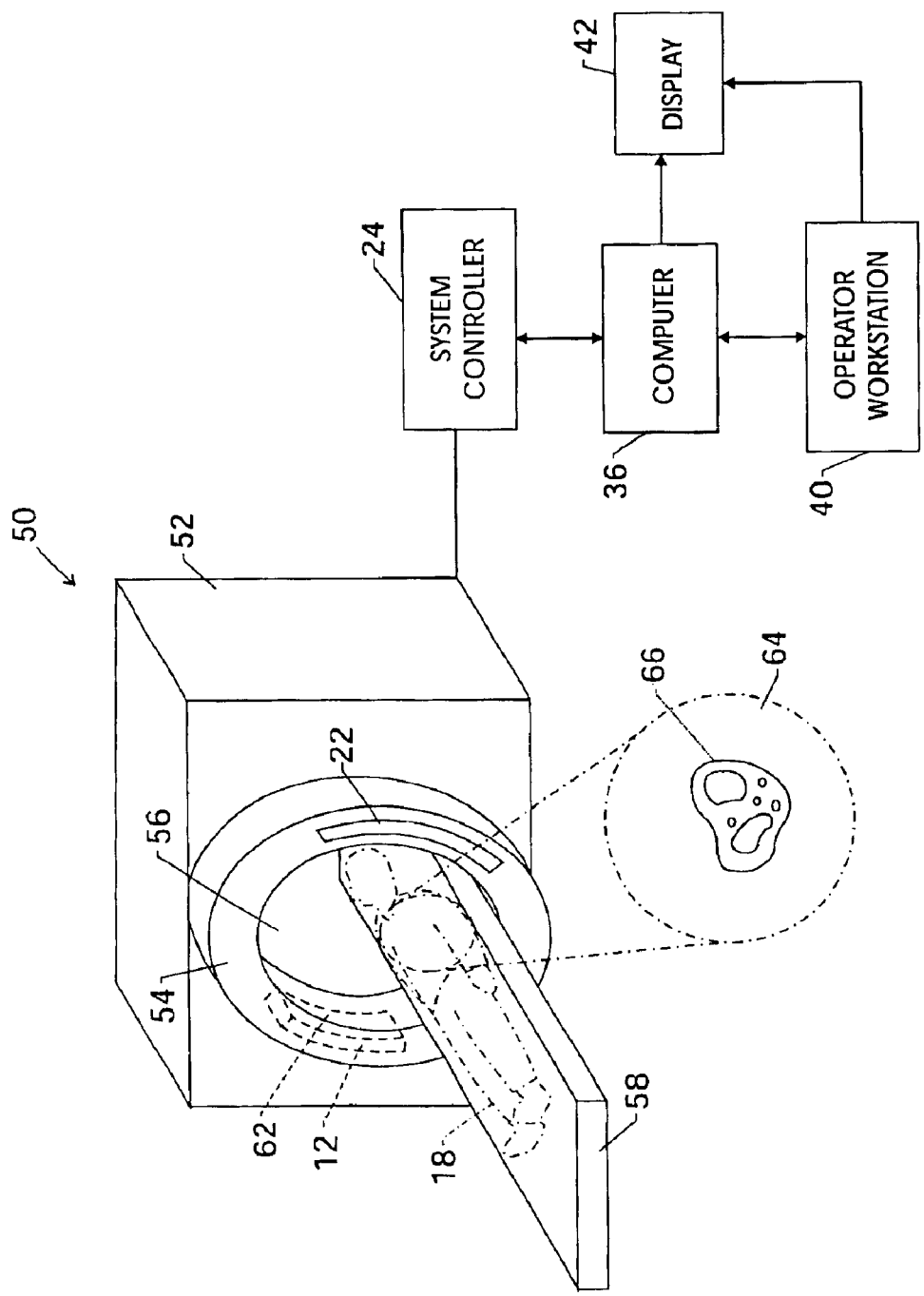
FIG. 2 is another diagrammatical view of a physical implementation of the CT system of FIG. 1, in accordance with one aspect of the present technique.

Referring generally to FIG. 2, an exemplary imaging system utilized in a present embodiment may be a CT scanning system 50. The CT scanning system 50 may be a multi-slice detector CT (MDCT) system that offers a wide array of axial coverage, high gantry rotational speed, and high spatial resolution. Alternately, the CT scanning system 50 may be a volumetric CT (VCT) system utilizing a cone-beam geometry and an area detector to allow the imaging of a volume, such as an entire internal organ of a subject, at high or low gantry rotational speeds. The CT scanning system 50 is illustrated with a frame 52 and a gantry 54 that has an aperture 56 through which a patient 18 may be moved. A patient table 58 may be positioned in the aperture 56 of the frame 52 and the gantry 54 to facilitate movement of the patient 18, typically via linear displacement of the table 58 by the linear positioning subsystem 26 (see FIG. 1). The gantry 54 is illustrated with the source of radiation 12, typically an X-ray tube that emits X-ray radiation from a focal point 62. For cardiac imaging, the stream of radiation is directed towards a cross section of the patient 18 including the heart.

In typical operation, X-ray source 12 projects an X-ray beam from the focal point 62 and toward detector array 22. The collimator 14 (see FIG. 1), such as lead or tungsten shutters, typically defines the size and shape of the X-ray beam that emerges from the X-ray source 12. The detector 22 is generally formed by a plurality of detector elements, which detect the X-rays that pass through and around a subject of interest, such as the heart or chest. Each detector element produces an electrical signal that represents the intensity of the X-ray beam at the position of the element at the time the beam strikes the detector. The gantry 54 is rotated around the subject of interest so that a plurality of radiographic views may be collected by the computer 36.

Thus, as the X-ray source 12 and the detector 22 rotate, the detector 22 collects data of the attenuated X-ray beams. Data collected from the detector 22 then undergoes pre-processing and calibration to condition the data to represent the line integrals of the attenuation coefficients of the scanned objects. The processed data, commonly called projections, may then be filtered and backprojected to formulate an image of the scanned area. A formulated image may incorporate, in certain modes, less or more than 360 degrees of projection data.

Once reconstructed, the cardiac image produced by the system of FIGS. 1 and 2 reveals the heart of the patient 18. As illustrated generally in FIG. 2, the image 64 may be displayed to show patient features, such as indicated at reference numeral 66 in FIG. 2. In traditional approaches for the diagnosis of disease states, and more generally of medical conditions or events, a radiologist or physician would consider the reconstructed image 64 to discern characteristic features of interest. Such features 66 include coronary arteries or stenotic lesions of interest, and other features, which would be discernable in the image, based upon the skill and knowledge of the individual practitioner. Other analyses may be based upon capabilities of various CAD algorithms.

As will be appreciated by those skilled in the art, reconstruction of an image 64 may be complicated by a variety of factors. For example, the CT system may acquire data continuously, although the signal in the detector elements is digitized at discrete angular positions, as the source and detector rotate about the subject. The resulting data set contains a large quantity of data points representative of the intensity of radiation impacting elements of the detector at each of the angular positions. For reasons of computational efficiency and to reduce the incidence of motion induced artifacts, it may be desirable to utilize only a subset, i.e., a projection data window or set, of the acquired data to formulate an image 64.

The projection data set is generally selected such that sufficient information is provided to calculate locations of features causing X-ray attenuation. For example, reconstruction of an image 64 may be accomplished using a half-scan reconstruction algorithm utilizing projection data acquired during rotation of the gantry encompassing 180° plus the included fan angle, $\alpha$, of the X-ray beam 16. Due to redundancy in data sets containing projection data acquired during a full rotation of the gantry, half-scan projection data sets generally suffice for image reconstruction and provide improved temporal resolution. Reconstruction may also be accomplished using multi-sector reconstruction techniques which employ a combination of shorter projection data sets, i.e., less than 180°+$\alpha$ which, in combination, provide the necessary data to reconstruct an image 64.

Reconstruction of images 64 of dynamically moving tissue may present particular concerns. For example, in the context of cardiac imaging, it is generally desirable to select projection data sets collected during the same cardiac phase, such as during a phase in which motion is minimized. Projection data sets that encompass data points acquired at different phases of the cardiac cycle may result in discontinuities or motion related artifacts in the reconstructed image or a rendered volume comprising a sequence of adjacent images.

Figure 3:
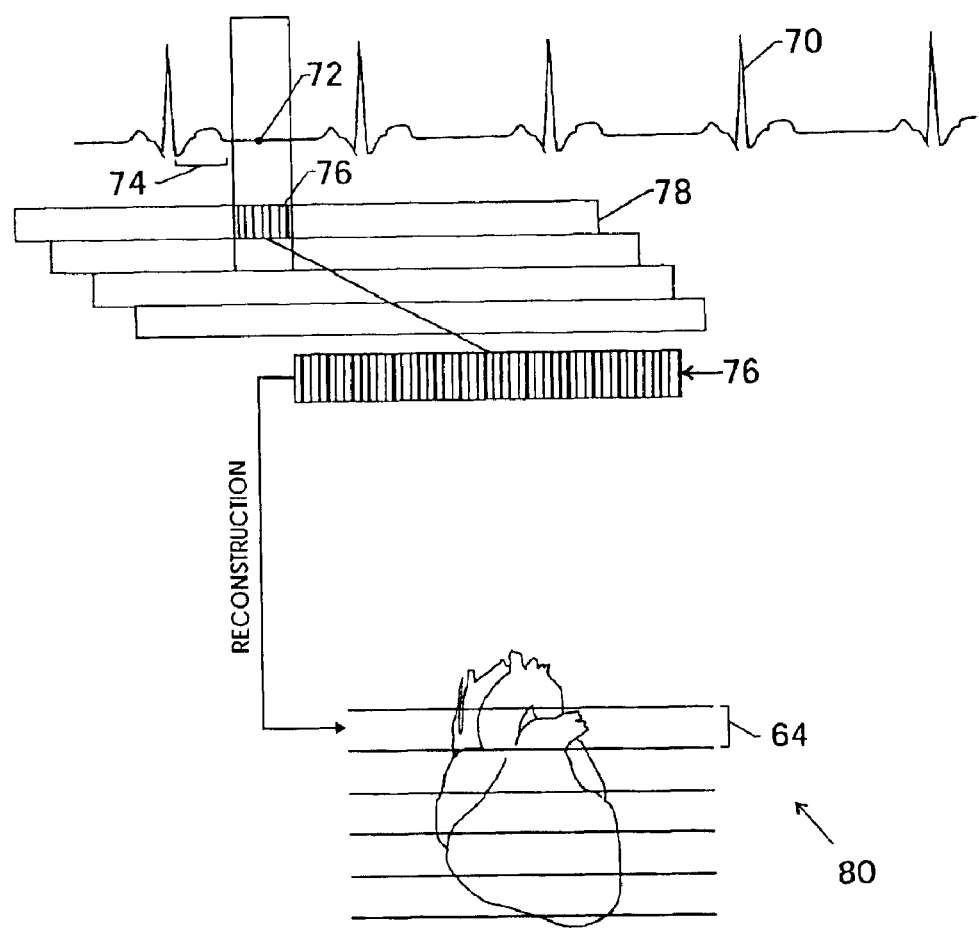
FIG. 3 is a representation of an ECG waveform used to retrospectively select acquired X-ray projection data to generate images used for reconstruction of a cardiac volume.

To address these motion-related issues it is generally desirable to extract cardiac phase information to assist in the selection of projection data sets. For example, simultaneously acquired electrocardiogram (ECG) data, such as the ECG waveform 70 depicted in FIG. 3, may be used as a general indicator of cardiac motion. In the depicted example, a point 72 on the waveform subsequent to the ST complex 74 may be used as an indicator of a relatively low motion phase of the cardiac cycle. The point 72 may therefore be used to select a projection data set 76 of the data acquired by a detector row 78. For example, in the depicted example, the projection data set 76 is a half-scan projection data set selected from the data acquired by a multi-slice detector CT system. The projection data set 76 may then be reconstructed to from an image 64, such as might comprise a volume rendering 80.

While conceptually the technique of using ECG data to select or "gate" the acquired projection data is straightforward, in practice the technique may be problematic in the clinical environment due to the additional burden of collecting simultaneous ECG data. Furthermore, the ECG data represents depolarization and repolarization of the cardiac muscle tissue, not the actual motion of the cardiac tissue. Therefore, the extent to which the ECG data accurately represents cardiac motion may vary. As a result, projection data sets selected based upon the ECG data may or may not be comprised of projection data acquired at the desired cardiac phase, meaning that motion-related artifacts and discontinuities may still be present in the reconstructed images.

Figure 4:
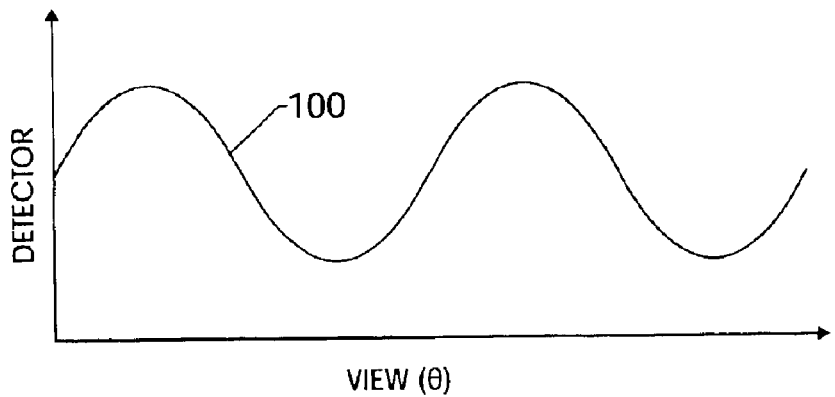
FIG. 4 is a representation of a sinogram derived from X-ray projection data.

One alternative to using ECG data to select projection data sets may be to utilize motion information inherent in the projection data itself to select projections acquired at the same cardiac phase. For example, sinogram consistency, as may be determined by the Helgason-Ludwig consistency conditions, may be used to determine the presence of motion within the projection data. As depicted in FIG. 4, a sinogram 100 is a two-dimensional dataset, p(s,θ), obtained by stacking the one-dimensional projections, $p_\theta(s)$, where θ is the view angle of data acquisition, and s is the detector element. For a static point in the imaging area, the sinogram 100, as one might expect, does indeed possess a sinusoidal form for a parallel beam X-ray source. Likewise, the sinogram 100 will deviate from a sinusoidal form in the presence of motion within the imaging area.

The structure of the sinogram 100 is governed by the Helgason-Ludwig consistency conditions, which state that a sinogram 100 may be decomposed into a number of moments, M, as given by the equation:

$$M_k(\theta) = \int s^k Rf(s,\theta) ds \qquad (1)$$

where k is a positive integer giving the order of the moment, s is the detector element, θ is the view angle, ƒ is the object function, and R is the Radon transform. The Helgason-Ludwig consistency conditions hold that the fan-beam sinogram-based moments, $M_k$, are homogeneous polynomials of degree or order, k, in sin θ and cos θ. As discussed in detail below, the various moments associated with the Helgason-Ludwig consistency conditions may be used to extract movement information from the projection data which may in turn be used to select projection data sets at the same cardiac phase or to otherwise facilitate image reconstruction of dynamically moving tissue.

Comparison of Reconstruction Sets Using Moments

One technique for projection data set selection uses Helgason-Ludwig consistency conditions to facilitate the selection of a single or multi-sector projection data set which most closely matches the motion characteristics of a reference projection data set. In particular, multi-sector reconstruction techniques may be preferred in instances where the rotation time of the gantry 54 differs from the heart rate of the patient such that there is no consistent correspondence between a view position and a phase of the cardiac cycle. The multi-sector projection data set may correspond to projection data acquired for an interval of 180°+α of gantry rotation, as with half-scan reconstruction. However, where a half-scan projection data set comprises a contiguous block of projection data, i.e., a single "sector," acquired during a single gantry rotation, the multi-sector projection data set is comprised of two or more sectors of projection data acquired during different rotations such that the end view angular position of one sector is sequentially adjacent to the beginning view angular position of the next sector.

Figure 5:
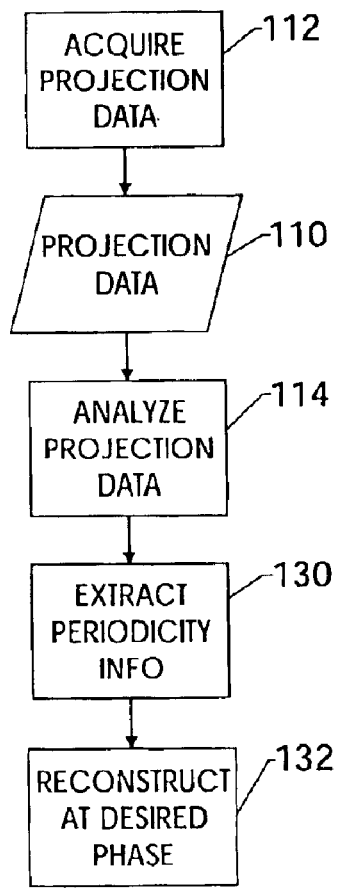
FIG. 5 is a flowchart depicting one technique of using consistency conditions to select data sets for reconstruction of images representative of dynamic tissue, in accordance with one aspect of the present technique.

In the present technique, projection data 110 is acquired, as depicted by step 112 of FIG. 5, such as by the helical operation of a multi-slice detector CT system or by operation of a volumetric CT system. The projection data associated with a z-location, i.e., axial slice, is analyzed over the available cardiac cycles at step 114. In the case of a helical acquisition, the projection data may include both the measured projection data as well as interpolated projection data generated by a helical interpolation technique, as is well known to those skilled in the art. All or part of the projection data may be analyzed, as described below. In particular, subsequent analysis may be limited to a subset of the projection data if the subset corresponding to the region of interest can be identified and extracted. Analysis of the subset of projection data may provide a superior signal-to-noise ratio in the region of interest compared to analysis of the full set of projection data.

Figure 6:
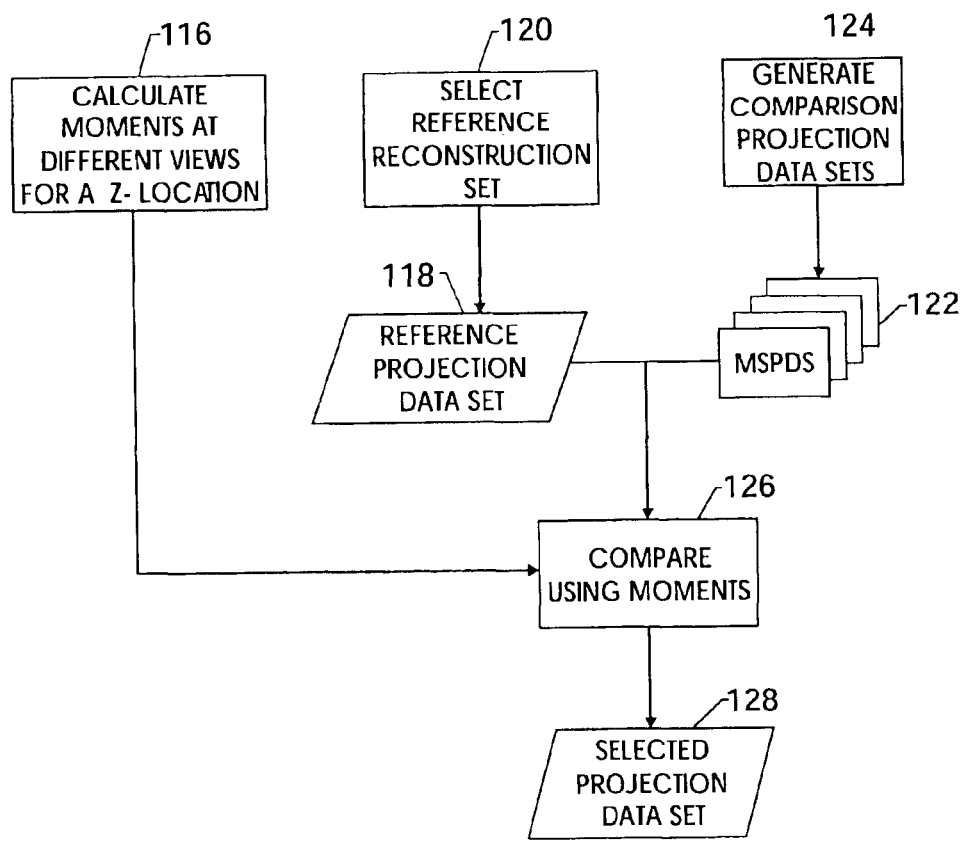
FIG. 6 is a flowchart depicting one technique for analyzing projection data, in accordance with one aspect of the present technique.

During the analysis, Helgason-Ludwig moments of one or more order may be calculated for the projection data 110 at the z-location for different projection data views, as depicted at step 116 of FIG. 6. For example, one or more of the $0^{th}$, 1st, or 2nd order moments may be calculated for each projection data view at the z-location. If moments of more than one order are calculated, the moments may be combined or kept separate for subsequent reference. The moments, either of an order or a combination of orders, may be plotted versus view position to provide a reduced representation of the motion within the projection data at the z-location. For example, the 0th order moments may be plotted as a function of view position for a z-location to generate one such reduced representation of motion.

A reference projection data set 118, such as a single sector or half-scan reconstruction set, may then be selected from the projection data at the z-location at step 120. Comparison projection data sets, such as multi-sector projection data sets (MSPDS) 122, are then generated at step 124. Each MSPDS 122 may be described by the number of sectors, N, comprising the MSPDS 122 and the offset, O, of the first view frame of the MSPDS 122 from the first view frame of the reference reconstruction set 118. The number of sector, N, therefore provides the number of gantry rotations used to acquire the data incorporated in to the MSPDS 122. Based on these factors, as many as N×O MSPDS 122 may be generated at step 124.

At step 126, the comparison projection data sets, here the MSPDS 122, may be compared to the reference projection data set 118 to determine which comparison sets are comprised of projections acquired at the same phase as the reference projection data set 118. In particular, the moment information calculated for each view frame at the z-location may be used to determine a correlation error that represents the difference between the projection data sets that may be attributed to motion, i.e., to phase differences. One method of obtaining a correlation error is to subtract the moments, such as the 0th order moments, associated with the projection data comprising a comparison projection data set 122 from the respective moments of the reference projection data set 118. For example, the 0th order moment of the first view of the MSPDS 122 may be subtracted from the 0th order moment of the first view of the reference projection data set 118, and so forth.

The sum of the absolute value of these differences, i.e., the correlation error, represents a measure of the difference between the projection data sets attributable to motion. The lower the correlation error, the less difference exists between the projection data sets due to motion, with a correlation error of zero indicating that no motion related differences exist. In other words, similar moments will be observed for the projection data sets if they are taken from the same phase of the cardiac cycle and thus little or no correlation error will be observed between the projection data sets. The correlation error may, therefore, be used to select the comparison projection set or sets 122 which most closely matches the reference projection data set 118, as depicted at step 126.

The selected projection data set 128 contains the projection information that characterizes cardiac period at one point in time. By repeating these steps as described below, the periodicity information may be used to extract the periodicity of the heart at that temporal neighborhood, as depicted at step 130 of FIG. 5. Using known information regarding patient motion in the z-direction along with the gantry rotation speed, the remainder of the axial cardiac slices may be reconstructed at the same phase to provide a volume rendering of the heart at that cardiac phase. Furthermore, the process described herein may be repeated for one or more other cardiac phases, allowing the cardiac motion during the entire scan to be obtained. Reconstruction of axial slices and/or cardiac volumes may then be performed at the desired phase, as depicted at step 132, without relying upon depolarization or repolarization data or other surrogate measures of cardiac motion.

Separation of a Motion Signal from a Corruptive Signal

Other techniques may also utilize consistency conditions, such as the Helgason-Ludwig consistency conditions, to generate useful motion information from the acquired projection data. The motion data may, in turn, be used in place of indirect measures of tissue motion, such as ECG data in the cardiac context. For example, the derived motion data may be used to facilitate data analysis or acquisition, such as for retrospective or prospective gating, respectively.

One problem that may arise, however, occurs when the period associated with the cardiac signal is similar to the rotational period associated with the CT gantry 54. For example, in a multi-slice detector CT system, the gantry rotation period may be on the order to 2 rotations per second while the patient's heart rate may on the order of 0.75 to 2 beats per second. In circumstances where the gantry rotation period and the cardiac period are close or overlap, the aggregate motion data may comprise not only the desired cardiac motion signal, but also a corruptive signal related to the data acquisition process. In particular, the 0th order moments of the Helgason-Ludwig consistency conditions generate low frequency modulations in the signal having the same period as the rotation period of the gantry.

One technique by which the corruptive and the motion signals may be separated is to rotate the gantry 54 at a velocity such that the rotational period is distinct from the cardiac period of the patient. For example, a sufficiently fast gantry rotation velocity may result in a corruptive motion component that is distinguishable from the cardiac motion component by frequency in either the temporal or the Fourier frequency domain. Similarly, slow gantry rotations, such as rotations that take three or more seconds for completion, may generate corruptive motion signals that can be separated from the cardiac motion components in the aggregate motion data by frequency characteristics.

For example, slow gantry rotations may be implemented on a volumetric CT system incorporating an area detector and cone-beam configuration. One benefit of the volumetric CT configuration is that, in a single rotation, projection data for the entire volume of the region of interest, such as the heart, is acquired at each view angle. The volumetric CT system, therefore, provides a higher signal-to-noise ratio than a multi-slice detector system because the entire volume of interest is within the field of view at each view position.

A volumetric CT system configured for slow gantry rotation, may therefore be used to acquire projection data. The projection data may be processed utilizing consistency relationships, such as the moments of the Helgason-Ludwig consistency conditions, to derive cardiac motion data from the projection data. For example, the Helgason-Ludwig 0th order moment corresponds to the sum of the line integrals of the linear attenuation coefficients for all the data acquired by the detector 22 at a view position. Generally, for a parallel beam geometry, a static object, and a monochromatic X-ray source, the 0th order moments should be equal for all view positions since the object is stationary and is identical for each view position. However, for a dynamic object, i.e., one undergoing motion within the field of view, the inconsistency of the projection data as a function of view position translates into variations in the 0th order moments. These variations correspond to the motion or change in configuration of the dynamic object within the field of view. The variations, therefore, may be analyzed to derive the motion of the dynamic object.

Figure 7:
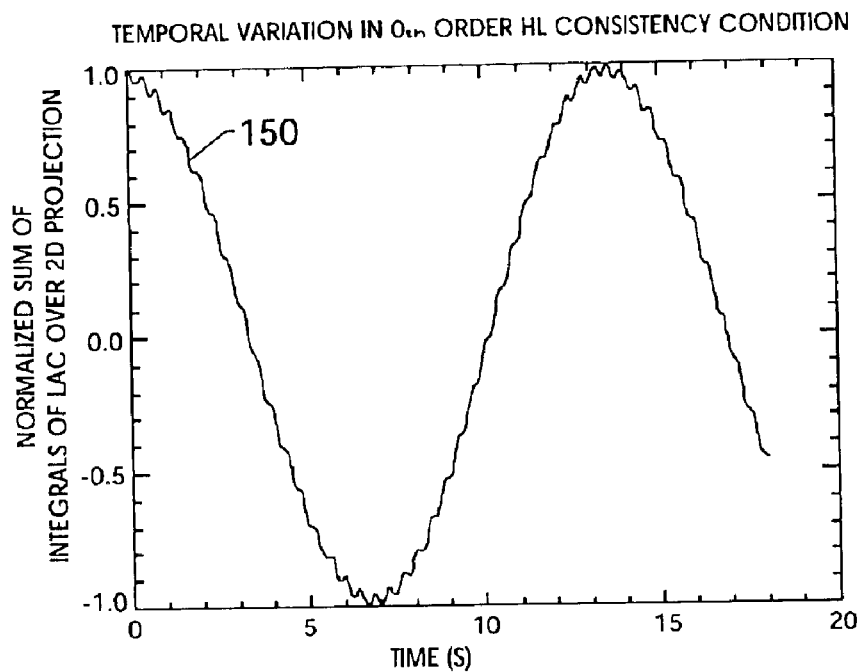
FIG. 7 is a chart depicting the approximate 0th order moment of a set of projection data acquired from a detector panel as a function of acquisition time, in accordance with one aspect of the present technique.

If the gantry has been slowly rotated while acquiring the projection data, the corruptive signal associated with gantry rotation may be separated from the desired motion signal, such as the cardiac motion signal, in the derived motion data, either in the temporal domain or the Fourier transform domain. For example, referring to FIG. 7, a signal representative of the 0th order moment 150 is shown. A low frequency component of the signal, resulting from the moment computation, and a high frequency component, resulting from motion of the heart during the cardiac cycle, are readily identifiable.

Figure 8:
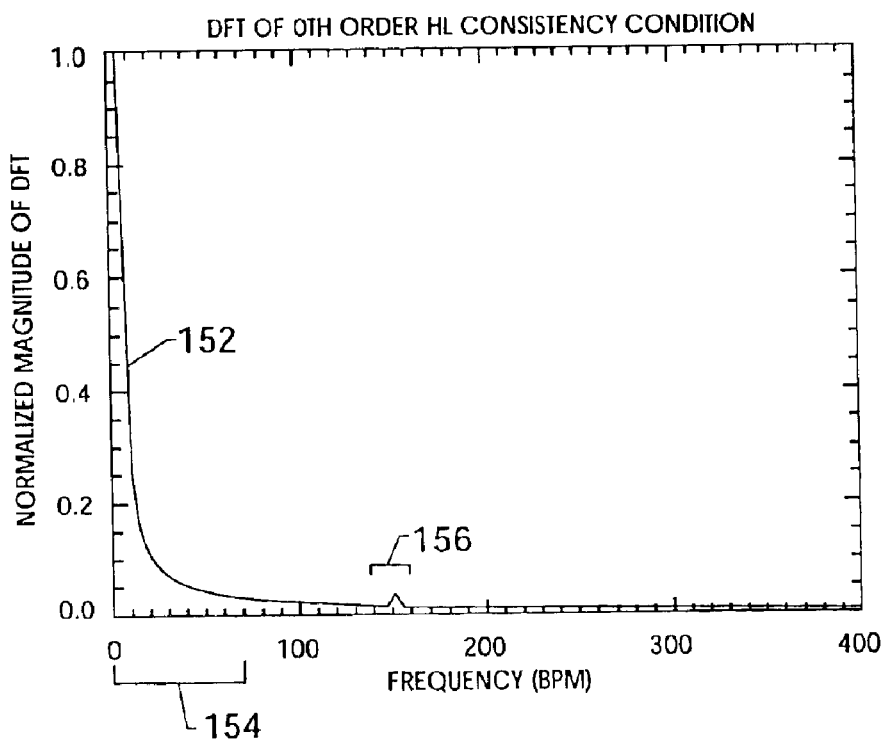
FIG. 8 is a chart depicting the magnitude of the discrete Fourier transform of the approximate 0th order moment of a set of projection data acquired at various view angle positions as a function of frequency, in accordance with one aspect of the present technique.

In FIG. 8, the magnitude of the discrete Fourier transform 152 of the 0th order moments of a projection data set acquired using a volumetric CT system with a detector rotating approximately once every 18 seconds is plotted against frequency. The low frequency artifacts 154 having a period related to the gantry rotation, i.e., approximately 3 rotations per minute, are easily distinguishable and separable from the cardiac portion 156 of the transform 152.

Figure 9:
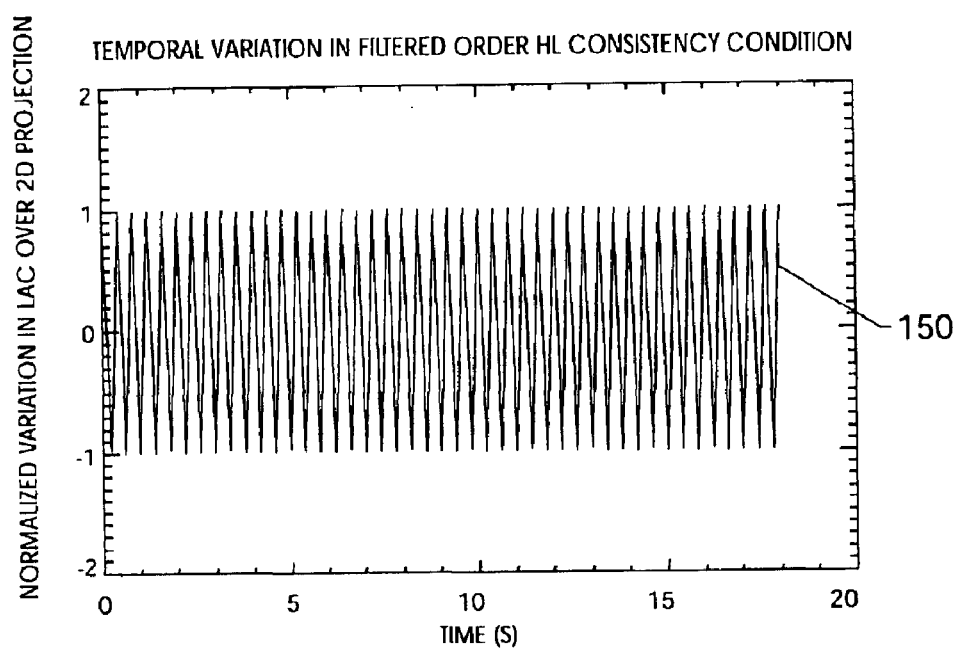
FIG. 9 is a chart depicting the filtered version of the approximate 0th order moment of a set of projection data acquired from a detector panel as a function of acquisition time, in accordance with one aspect of the present technique.

After separation of the corruptive signal, i.e., low frequency artifacts 152, the 0th order moments as a function of view frame may be analyzed to derive the motion of the tissue within the field of view over time. For example, referring to FIG. 9, the 0th order moments 150 are plotted against time to display the cardiac motion of the imaged heart during the scan interval. From this information, the periodicity of the heart may be determined and used in the reconstruction of the projection data, such as for gating, to reconstruct images at the desired cardiac phase.

Furthermore, if the approximate subset of the field of view associated with the volume of interest, such as the heart, is identified, the projection data associated with those subsets may be used to generate the aggregate motion data signal. By limiting analysis to the subset of projection data, the fidelity of the desired motion signal, such as the cardiac signal, may be further increased relative to the corruptive component. For example, this subsetting process may be accomplished by estimating the subregion within the total field of view of the imaging system that encompasses the heart or other organ and identifying the shadow of this estimated region on the detector 22 for each view position of the gantry 54. By means of this process, further refinement of the desired motion signal may be achieved. The motion signal may, in turn be used to reconstruct images at a desired cardiac phase or to otherwise facilitate temporally resolved reconstruction or acquisition of projection data of dynamic tissue.

As one of ordinary skill in the art will appreciate, the processes described herein may be provided as one or more routines executable by the computer 36 or by other processor-based components of the CT system 10. The routines may be stored or accessed on one or more computer-readable media, such as magnetic or optical media, which may be local to the computer 36 or processor-based component or may be remotely accessible via a network connection, such as via the Internet or a local area network. Furthermore, access to or operation of the routines may be provided to an operator via the operator workstation 40 as part of the normal operation of a CT imaging system 10.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for selecting a projection data set, comprising:
    (a) acquiring a set of projection data;
    (b) calculating at least one set of the 0th order moments, the 1st order moments, and the 2nd order moments of the set of projection data at different views positions for an axial location;
    (c) selecting a reference projection data set from the projection data at the axial location;
    (d) generating two or more comparison projection data sets from the projection data at the axial location;
    (e) deriving a correlation error for each comparison projection data set relative to the reference projection data set using the at least one set of moments; and
    (f) selecting a matching projection data set based upon the correlation errors.

2. The method as recited in claim 1, wherein the set of projection data is acquired with a multi-slice CT detector system.

3. The method as recited in claim 1, wherein the set of projection data is acquired with a volumetric CT detector system.

4. The method as recited in claim 1, wherein the set of projection data comprises a set of cardiac projection data.

5. The method as recited in claim 1, wherein calculating the moments is performed at all view positions.

6. The method as recited in claim 1, wherein the reference projection data set comprises a half-scan projection data set.

7. The method as recited in claim 1, wherein the comparison projection data sets comprise multi-sector projection data sets.

8. The method as recited in claim 7, wherein up to N×O multi-sector projection data sets are generated.

9. The method as recited in claim 1, wherein the correlation error is derived by summing the absolute values of the differences between the moments of the reference projection data set and the respective moments of the comparison projection data set at comparable view positions.

10. The method as recited in claim 1, wherein the matching projection data set is selected which has the lowest correlation error.

11. The method as recited in claim 1, further comprising reconstructing an image from the matching projection data set.

12. The method as recited in claim 1, further comprising extracting periodicity information from the matching projection data sets or from an image reconstructed from the matching projection data sets.

13. The method as recited in claim 12, further comprising reconstructing one or more images from the set of projection data using the periodicity information.

14. The method as recited in claim 1, further comprising repeating steps (b) through (f) for additional axial locations.

15. The method as recited in claim 14, further comprising reconstructing an image for each matching projection data set.

16. The method as recited in claim 15, further comprising rendering a volume comprising the images.

17. The method as recited in claim 14, further comprising extracting periodicity information from the matching projection data sets or from images reconstructed from the matching projection data sets.

18. The method as recited in claim 17, further comprising reconstructing one or more images from the set of projection data using the periodicity information.

19. A computer program, provided on one or more computer readable media, for selecting a projection data set, comprising:
    a routine for acquiring a set of projection data;
    a routine for calculating at least one set of the 0th order moments, the 1st order moments, and the 2nd order moments of the set of projection data at different views positions for an axial location;
    a routine for selecting a reference projection data set from the projection data at the axial location;
    a routine for generating two or more comparison projection data sets from the projection data at the axial location;
    a routine for deriving a correlation error for each comparison projection data set relative to the reference projection data set using the at least one set of moments; and
    a routine for selecting a matching projection data set based upon the correlation errors.

20. The computer program as recited in claim 19, wherein the set of projection data comprises a set of cardiac projection data.

21. The computer program as recited in claim 19, wherein the routine for calculating the moments calculates the moments at all view positions.

22. The computer program as recited in claim 19, wherein the reference projection data set comprises a half-scan projection data set.

23. The computer program as recited in claim 19, wherein the comparison projection data sets comprise multi-sector projection data sets.

24. The computer program as recited in claim 23, wherein the routine generates up to N×O multi-sector projection data sets.

25. The computer program as recited in claim 19, wherein the routine for deriving a correlation error sums the absolute values of the differences between the moments of the reference projection data set and the respective moments of the comparison projection data set at comparable view positions.

26. The computer program as recited in claim 19, wherein the routine for selecting a matching projection data set selects the matching projection data set which has the lowest correlation error.

27. The computer program as recited in claim 26, further comprising a routine for reconstructing an image from the matching projection data set.

28. The computer program as recited in claim 19, further comprising a routine for extracting periodicity information from the matching projection data sets or from an image reconstructed from the matching projection data sets.

29. The computer program as recited in claim 28, further comprising a routine for reconstructing one or more images from the set of projection data using the periodicity information.

30. The computer program as recited in claim 29, further comprising a routine for rendering a volume from two or more reconstructed images.

31. A CT image analysis system comprising:
an X-ray source configured to emit a stream of radiation;
a detector configured to detect the stream of radiation and to generate one or more signals responsive to the stream of radiation, wherein the detector comprises a plurality of detector elements;
a system controller configured to control the X-ray source and to acquire a set of projection data from one or more of the detector elements via a data acquisition system; and
a computer system configured to receive the set of projection data, to calculate at least one set of the 0th order moments, the 1st order moments, and the 2nd order moments of the set of projection data at different views positions for an axial location, to select a reference projection data set from the projection data at the axial location, to generate two or more comparison projection data sets from the projection data at the axial location, to derive a correlation error for each comparison projection data set relative to the reference projection data set using the at least one set of moments, and to select a matching projection data set based upon the correlation errors.

32. The CT image analysis system as recited in claim 31, wherein the detector comprises a multi-slice CT detector.

33. The CT image analysis system as recited in claim 31, wherein the detector comprises a volumetric CT detector.

34. The CT image analysis system as recited in claim 31, wherein the set of projection data comprises a set of cardiac projection data.

35. The CT image analysis system as recited in claim 31, wherein the computer calculates the moments at all view positions.

36. The CT image analysis system as recited in claim 31, wherein the comparison projection data sets comprise multi-sector projection data sets, and wherein the computer is configured to generate up to N×O multi-sector projection data sets.

37. The CT image analysis system as recited in claim 31, wherein the computer derives the correlation error by summing the absolute values of the differences between the moments of the reference projection data set and the respective moments of the comparison projection data set at comparable view positions.

38. The CT image analysis system as recited in claim 31, wherein the computer selects the matching projection data set which has the lowest correlation error.

39. The CT image analysis system as recited in claim 31, wherein the computer is further configured to reconstruct an image from the matching projection data set.

40. The CT image analysis system as recited in claim 31, wherein the computer is further configured to extract periodicity information from the matching projection data sets or from an image reconstructed from the matching projection data sets.

41. The CT image analysis system as recited in claim 40, wherein the computer is further configured to reconstruct one or more images from the set of projection data using the periodicity information.

42. The CT image analysis system as recited in claim 41, wherein the computer is further configured to render a volume from two or more reconstructed images.

43. A CT image analysis system comprising:
an X-ray source configured to emit a stream of radiation;
a detector configured to detect the stream of radiation and to generate one or more signals responsive to the stream of radiation, wherein the detector comprises a plurality of detector elements;
a system controller configured to control the X-ray source and to acquire a set of projection data from one or more of the detector elements via a data acquisition system;
a computer system configured to receive the set of projection data;
means for calculating at least one set of moments of the set of projection data at different views positions for an axial location;
means for selecting a reference projection data set from the projection data at the axial location;
means for generating two or more comparison projection data sets from the projection data at the axial location;
means for deriving a correlation error for each comparison projection data set relative to the reference projection data set using the at least one set of moments; and
means for selecting a matching projection data set based upon the correlation errors.

44. The CT image analysis system as recited in claim 43, further comprising means for reconstructing an image from the matching projection data set.

45. The CT image analysis system as recited in claim 43, further comprising means for reconstructing one or more images from the set of projection data using periodicity information extracted from the matching projection data sets or from an image reconstructed from the matching projection data sets.

46. A method for generating a motion signal from a set of projections, comprising:
acquiring a set of projection data, wherein the set of projection data is acquired by a slowly rotating area detector and cone-beam radiation source;
calculating the 0th order moments for the set of projection data for each view position to form an aggregate motion signal; and
separating the aggregate motion signal into a corruptive signal and a desired motion signal based on frequency characteristics.

47. The method as recited in claim 46, wherein a rotation of the area detector and cone-beam radiation source takes more than 3 seconds.

48. The method as recited in claim 47, wherein the rotation takes 18 seconds or more.

49. The method as recited in claim 46, wherein separating the aggregate signal occurs in the temporal domain.

50. The method as recited in claim 46, wherein separating the aggregate signal occurs in the Fourier transform domain after performing a Fourier transformation of the 0th order moments.

51. The method as recited in claim 46, wherein the desired motion signal is a cardiac motion signal.

52. The method as recited in claim 51, further comprising reconstructing one or more images based upon the desired motion signal.

53. The method as recited in claim 46, wherein the set of projection data is a subset of the total projection data.

54. The method as recited in claim 53, wherein the set of projection data comprises those projections associated with a volume of interest in the field of view.

55. The method as recited in claim 54, wherein the volume of interest comprises a volume associated with an internal organ.

56. The method as recited in claim 55, wherein the internal organ is a heart.

57. A computer program, provided on one or more computer readable media, for generating a motion signal from a set of projections, comprising:

a routine for acquiring a set of projection data using a slowly rotating area detector and cone-beam radiation source;

a routine for calculating the 0th order moments for the set of projection data for each view position to form an aggregate motion signal; and a routine for separating the aggregate motion signal into a corruptive signal and a desired motion signal based on frequency characteristics.

58. The computer program as recited in claim 57, wherein the routine for separating the aggregate motion signal separates the aggregate motion signal in the temporal domain.

59. The computer program as recited in claim 57, wherein the routine for separating the aggregate motion signal separates the aggregate motion signal in the Fourier transform domain after performing a Fourier transformation of the 0th order moments.

60. The computer program as recited in claim 57, further comprising a routine for reconstructing one or more images based upon the desired motion signal.

61. A CT image analysis system, comprising:

a cone-beam X-ray source configured to emit a stream of radiation;

an area detector configured to detect the stream of radiation and to generate one or more signals responsive to the stream of radiation, wherein the detector comprises a plurality of detector elements;

a system controller configured to slowly rotate the cone-beam X-ray source and the area detector and to acquire a set of projection data from one or more of the detector elements via a data acquisition system; and a computer system configured to receive the set of projection data, to calculate the 0th order moments for the set of projection data for each view position to form an aggregate motion signal and to separate the aggregate motion signal into a corruptive signal and a desired motion signal based on frequency characteristics.

62. The CT image analysis system as recited in claim 61, wherein a rotation of the area detector and cone-beam radiation source takes more than 3 seconds.

63. The CT image analysis system as recited in claim 62, wherein a rotation of the area detector and cone-beam radiation source takes 18 seconds or more.

64. The CT image analysis system as recited in claim 61, wherein the computer system is configured to separate the aggregate motion signal in the temporal domain.

65. The CT image analysis system as recited in claim 61, wherein the computer system is configured to separate the aggregate motion signal in the Fourier transform domain after performing a Fourier transformation of the 0th order moments.

66. The CT image analysis system as recited in claim 61, wherein the computer system is further configured to reconstructing one or more images based upon the desired motion signal.

67. A CT image analysis system, comprising:

a cone-beam X-ray source configured to emit a stream of radiation;

an area detector configured to detect the stream of radiation and to generate one or more signals responsive to the stream of radiation, wherein the detector comprises a plurality of detector elements;

a system controller configured to slowly rotate the cone-beam X-ray source and the area detector and to acquire a set of projection data from one or more of the detector elements via a data acquisition system;

a computer system configured to receive the set of projection data;

means for forming an aggregate motion signal; and means for separating the aggregate motion signal into a corruptive signal and a desired motion signal based on frequency characteristics.

68. The CT image analysis system as recited in claim 67, further comprising means for reconstructing one or more images based upon the desired motion signal.

* * * * *